US005739356A

United States Patent [19]
Dietz et al.

[11] Patent Number: 5,739,356
[45] Date of Patent: Apr. 14, 1998

[54] LACTONES USEFUL AS INTERMEDIATES FOR PREPARING LUBRICATING OIL AND FUEL ADDITIVES

[75] Inventors: Jeffry G. Dietz, University Heights; Mark R. Baker, Lyndhurst; Paul E. Adams, Willoughby Hills, all of Ohio

[73] Assignee: The Lubrizol Corporation, Wickliffe, Ohio

[21] Appl. No.: 754,639

[22] Filed: Nov. 21, 1996

Related U.S. Application Data

[62] Division of Ser. No. 517,893, Aug. 22, 1995, abandoned.

[51] Int. Cl.$^6$ ................................................. C07D 493/04
[52] U.S. Cl. ........................... 549/285; 549/283; 549/306
[58] Field of Search ................................. 549/283, 285, 549/306

[56] References Cited

U.S. PATENT DOCUMENTS

| | | | |
|---|---|---|---|
| 3,172,892 | 3/1965 | LeSuer et al. | 260/326.5 |
| 3,215,707 | 11/1965 | Rense | 260/326.3 |
| 3,454,607 | 7/1969 | LeSuer et al. | 260/408 |
| 4,103,023 | 7/1978 | Aldridge et al. | 549/306 |
| 4,412,031 | 10/1983 | Kitahara et al. | 524/526 |
| 4,412,041 | 10/1983 | Kitahara et al. | 525/154 |
| 4,525,541 | 6/1985 | Kitahara et al. | 525/337 |
| 4,654,435 | 3/1987 | Kitahara et al. | 560/61 |
| 4,704,427 | 11/1987 | Kitahara et al. | 524/531 |

FOREIGN PATENT DOCUMENTS

| | | |
|---|---|---|
| 2103686 | 8/1972 | Germany. |
| WO 95/31488 | 11/1995 | WIPO. |

OTHER PUBLICATIONS

Mukiayama et al., Bull. J Chem. Soc. of Japan, vol. 44, pp. 161–166, 1971.
B.B. Snider et al., J. Org. Chem. 44, 3567 (1979).
B.B. Jarvis et al., Synthesis, 11, 1079 (1990).
K. Mikami et al., Tetrahedron Letters 35, 3133 (1994).
M. Terada et al., J. Chem. Soc. Chem. Commun., 833 (1994).
I.M. Akhmedov et al., Synthetic Communications, 24, 137 (1994).
K. Mikami et al., Chem. Rev. 92, 1021 (1992).
M. Terada et al., Tetrahedron Letters, 35, 6693 (1994).
D. Savostianoff, C.R. Acad. Sc. Paris, 263, 605 (Aug. 22, 1966).
M. Kerfanto et al., C.R. Acad. Sc. Paris, 264, 232 (1967).

*Primary Examiner*—Bernard Dentz
*Attorney, Agent, or Firm*—Joseph P. Fischer; James L. Cordek

[57] ABSTRACT

A process for preparing compounds useful as intermediates used for preparing lubricant and fuel additives. The intermediates include the products prepared by the process and dilactones.

58 Claims, No Drawings

LACTONES USEFUL AS INTERMEDIATES FOR PREPARING LUBRICATING OIL AND FUEL ADDITIVES

This application is a Divisional of application Ser. No. 08/517,893, filed Aug. 22, 1995, now abandoned.

FIELD OF THE INVENTION

This invention relates to a process for preparing compositions which are useful as intermediates for the preparation of low chlorine containing additives for lubricating oils and normally liquid fuels, compounds prepared by the process, and dilactone compounds.

BACKGROUND OF THE INVENTION

Numerous types of additives are used to improve lubricating oil and fuel compositions. Such additives include, but are certainly not limited to dispersants and detergents of the ashless and ash-containing variety, oxidation inhibitors, anti-wear additives, friction modifiers, and the like. Such materials are well known in the art and are described in many publications, for example, Smalheer, et al,"Lubricant Additives", Lezius-Hiles Co., Cleveland, Ohio, USA (1967); M. W. Ranney, Ed., "Lubricant Additives", Noyes Data Corp., Park Ridge, N.J., USA (1973); M. J. Satriana, Ed., "Synthetic Oils and Lubricant Additives, Advances since 1979", Noyes Data Corp., Park Ridge N.J., USA (1982), W. C. Gergel, "Lubricant Additive Chemistry", Publication 694-320-65R1 of the Lubrizol Corp. , Wickliffe, Ohio, USA (1994); and W. C. Gergel et al, "Lubrication Theory and Practice" Publication 794-320-59R3 of the Lubrizol Corp., Wickliffe, Ohio, USA (1994); and in numerous United States patents, for example Chamberlin, III, U.S. Pat. No. 4,326, 972, Schroeck et al, U.S. Pat. No. 4,904,401, and Ripple et al, U.S. Pat. No. 4,981,602. Many such additives are frequently derived from carboxylic reactants, for example, acids, esters, anhydrides, lactones, and others. Specific examples of commonly used carboxylic compounds used as intermediates for preparing lubricating oil additives include alkyl-and alkenyl substituted succinic acids and anhydrides, polyolefin substituted carboxylic acids, aromatic acids, such as salicylic acids, and others. Illustrative carboxylic compounds are described in Meinhardt, et al, U.S. Pat. No. 4,234,435; Norman et al, U.S. Pat. No. 3,172,892; LeSuer et al, U.S. Pat. No. 3,454,607 and Rense, U.S. Pat. No. 3,215,707.

Many carboxylic intermediates used in the preparation of lubricating oil additives contain chlorine. While the amount of chlorine present is often only a very small mount of the total weight of the intermediate, the chlorine frequently is carried over into the carboxylic derivative which is desired as an additive. For a variety of reasons, including environmental reasons, the industry has been making efforts to reduce or to eliminate chlorine from additives designed for use as lubricant or fuel additives.

Accordingly, it is desirable to provide low chlorine or chlorine free intermediates which can be used to prepare low chlorine or chlorine free derivatives for use in lubricants and fuels.

The present invention provides a process and products prepared by the process and also dilactones which meet this requirement.

B. B. Snider and J. W. van Straten, J. Org. Chem., 44, 3567–3571 (1979) describe certain products prepared by the reaction of methyl glyoxylate with several butenes and cyclohexenes. K. Mikami and M. Shimizu, Chem. Rev., 92, 1021–1050 (1992) describe carbonyl-ene reactions, including glyoxylate-ene reactions. D. Savostianov (communicated by P. Pascal), C. R. Acad. Sc. Paris, 263, (605–7) (1966) relates to preparation of some α-hydroxylactones via the action of glyoxylic acid on olefins. M. Kerfanto et. al., C. R. Acad. Sc. Paris, 264, (232–5) (1967) relates to condensation reactions of α-α-di-(N-morpholino) acetic acid and glyoxylic acid with olefins. B. B. Jarvis et al, Synthesis, 1079–82 (1990) relates to reactions of oxocarboxylic acids with olefins under acidic conditions to give α-hydroxy butyrolactones.

SUMMARY OF THE INVENTION

This invention provides a process for reacting, usually in the presence of an acidic catalyst, (A) at least one olefinic compound of the general formula

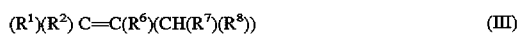

wherein each of $R^1$ and $R^2$ is, independently, hydrogen or a hydrocarbon based group and each of $R^6$, $R^7$ and $R^8$ is, independently, hydrogen or a hydrocarbon based group, and (B) at least one carboxylic reactant selected from the group consisting of compounds of the formula

and compounds of the formula

wherein each of $R^3$, $R^5$ and $R^9$ is independently H or a hydrocarbyl group, $R^4$ is a divalent hydrocarbylene group, and n is 0 or 1, wherein the reactants are reacted in amounts ranging from more than 1.5 moles up to about 3 moles (B) per equivalent of (A), wherein equivalents of (A) are defined hereinafter.

Products prepared by this process are also provided.

The present invention also provides a composition comprising regiosomers selected from the group consisting of

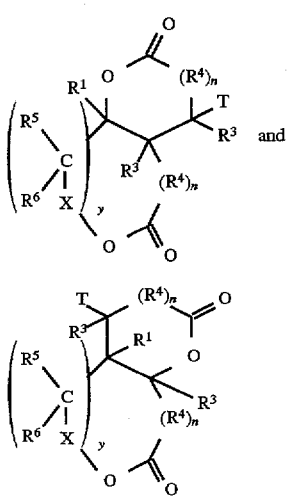

wherein each $R^1$ is H or a hydrocarbon based group, each $R^3$ is H or hydrocarbyl;

each $R^4$ is a divalent hydrocarbylene group;
each n=0 or 1;
y=0 or 1;
wherein X is a divalent hydrocarbyl group selected from the group consisting of
>C($R^6$)(C($R^5$)($R^7$)($R^8$)) when y=0, and
>C($R^7$)($R^8$) when y=1
each $R^5$ is H or hydrocarbyl; and
each of $R^6$, $R^7$ and $R^8$ is independently H or a hydrocarbon based group, and T is selected from the group consisting of —OH and $R^5$.

DETAILED DESCRIPTION OF THE PREFERRED EMBODIMENTS

As used herein, the terms "hydrocarbon", "hydrocarbyl" or "hydrocarbon based" mean that the group being described has predominantly hydrocarbon character within the context of this invention. These include groups that are purely hydrocarbon in nature, that is, they contain only carbon and hydrogen. They may also include groups containing substituents or atoms which do not alter the predominantly hydrocarbon character of the group. Such substituents may include halo-, alkoxy-, nitro-, etc. These groups also may contain hetero atoms. Suitable hetero atoms will be apparent to those skilled in the art and include, for example, sulfur, nitrogen and oxygen. Therefore, while remaining predominantly hydrocarbon in character within the context of this invention, these groups may contain atoms other than carbon present in a chain or ring otherwise composed of carbon atoms.

In general, no more than about three non-hydrocarbon substituents or hetero atoms, and preferably no more than one will be present for every 10 carbon atoms in the hydrocarbon, hydrocarbyl or hydrocarbon based groups. Most preferably, the groups are purely hydrocarbon in nature, that is they are essentially free of atoms other than carbon and hydrogen.

Throughout the specification and claims the expression oil soluble or dispersible is used. By oil soluble or dispersible is meant that an amount needed to provide the desired level of activity or performance can be incorporated by being dissolved, dispersed or suspended in an oil of lubricating viscosity. Usually, this means that at least about 0.001% by weight of the material can be incorporated in a lubricating oil. For a further discussion of the terms oil soluble and dispersible, particularly "stably dispersible", see U.S. Pat. No. 4,320,017 which is expressly incorporated herein by reference for relevant teachings in this regard.

As noted hereinabove, provided by this invention is a process for preparing low chlorine or chlorine free compositions useful as intermediates for preparing low chlorine or chlorine free additives for lubricating oil and fuel compositions.

The Process

The present invention relates to a process comprising reacting, usually in the presence of an acidic catalyst, more than 1.5 moles, preferably from about 1.6 to about 3 moles of (B) at least one carboxylic reactant per equivalent of (A) at least one olefinic compound wherein (A) and (B) are defined in greater detail hereinbelow.

All of the reactants may be present at the same time. It has been found that improvements in yield and purity of product are sometimes attained when the carboxylic reactant (B) is added portionwise over an extended period of time, usually up to about 10 hours, more often from 1 hour up to about 6 hours, frequently from about 2–4 hours. However, it is generally preferred to have all of the reactants present at the outset. Water is removed during reaction.

Optionally the process may be conducted in the presence of a solvent. Well known solvents include aromatic and aliphatic solvents, oil, etc. When a solvent is used, the mode of combining reactants does not appear to have any effect.

The Catalyst

The process of this invention is optionally conducted in the presence of an acidic catalyst. Acid catalysts, such as organic sulfonic acids, for example, paratoluene sulfonic acid and methane sulfonic acid, heteropolyacids, the complex acids of heavy metals (e.g., Mo, W, Sn, V, Zr, etc.) with phosphoric acids (e.g., phosphomolybdic acid), and mineral acids, for example, $H_2SO_4$ and phosphoric acid, are useful. The amount of catalyst used is generally small, ranging from about 0.01 mole % to about 10 mole %, more often from about 0.1 mole % to about 2 mole %, based on moles of olefinic reactant.

(A) The Olefinic Compound

The olefinic compound employed as a reactant in the process of this invention has the general formula $$(R^1)(R^2)C=C(R^6)(CH(R^7)(R^8)) \quad (III)$$

wherein each of $R^1$ and $R^2$ is, independently, hydrogen or a hydrocarbon based group and each of $R^6$, $R^7$ and $R^8$ is, independently, hydrogen or a hydrocarbon based group provided that at least one is a hydrocarbon based group containing at least 7 carbon atoms. These olefinic compounds are diverse in nature.

Virtually any compound containing an olefinic bond may be used provided it meets the general requirements set forth hereinabove for (III) and does not contain any functional groups (e.g., primary or secondary amines) that would interfere with the carboxylic reactant (B). Useful olefinic compounds may be terminal olefins, i.e., olefins having a

group, or internal olefins. Useful olefinic compounds may have more than one olefinic bond, i.e., they may be dienes, trienes, etc. Most often they are mono-olefinic. Examples include linear ∝-olefins, cis- or trans- disubstituted olefins, trisubstituted olefins and tetrasubstituted olefins.

When (A) is a mono-olefin, one mole of (A) contains one equivalent of C=C; when (A) is a di-olefin, one mole of (A) contains 2 equivalents of C=C bonds; when (A) is a tri-olefin, one mole of (A) contains 3 equivalents of C=C bonds, and so forth.

Aromatic double bonds are not considered to be olefinic double bonds within the context of this invention.

As used herein, the expression "polyolefin" defines a polymer derived from olefins. The expression "polyolefinic" refers to a compound containing more than one C=C bond.

Among useful compounds are those that are purely hydrocarbon, i.e., those substantially free of non-hydrocarbon groups, or they may contain one or more non-hydrocarbon groups as discussed in greater detail herein.

In one embodiment, the olefinic compounds are substantially hydrocarbon, that is, each R group in (III) is H or contains essentially carbon and hydrogen. In one aspect within this embodiment, each of $R^1$, $R^2$, $R^7$ and $R^8$ is hydrogen and $R^6$ is a hydrocarbyl group, frequently containing from 7 to about 5,000 carbon atoms, more often from about 30 up to about 200 carbon atoms, preferably from about 50 up to about 100 carbon atoms. In another aspect of this embodiment, each of $R^1$ and $R^2$ is hydrogen, $R^6$ is H or a lower alkyl group and the group $(CH(R^7)(R^8))$ is a hydrocarbyl group, frequently containing from 7 to about 5,000 carbon atoms, more typically from about 30 up to about 200 carbon atom, preferably from 50 up to about 100 carbon atoms.

In another embodiment, one or more of the R groups present in (III) is an organic radical which is not purely hydrocarbon. Such groups may contain or may be groups such as carboxylic acid, ester, amide, salt, including ammonium, amine and metal salts, cyano, hydroxy, thiol, tertiary amino, nitro, alkali metal mercapto and the like. Illustrative of olefinic compounds (III) containing such groups are methyl oleate, oleic acid, 2-dodecenedioic acid, octene diol, linoleic acid and esters thereof, and the like.

Preferably, the hydrocarbyl groups are aliphatic groups. In one preferred embodiment, when an R group is an aliphatic group containing a total of from about 30 to about 100 carbon atoms, the olefinic compound is derived from homopolymerized and interpolymerized $C_{2-18}$ mono- and di-olefins, preferably 1-olefins. In a preferred embodiment, the olefins contain from 2 to about 5 carbon atoms, preferably 3 or 4 carbon atoms. Examples of such olefins are ethylene, propylene, butene-1, isobutylene, butadiene, isoprene, 1-hexene, 1-octene, etc. R groups can, however, be derived from other sources, such as monomeric high molecular weight alkenes (e.g. 1-tetracontene), aliphatic petroleum fractions, particularly paraffin waxes and cracked analogs thereof, white oils, synthetic alkenes such as those produced by the Ziegler-Natta process (e.g., poly-(ethylene) greases) and other sources known to those skilled in the art. Any unsaturation in the R groups may be reduced by hydrogenation according to procedures known in the art, provided at least one olefinic group remains as described for (III).

In one preferred embodiment, at least one R is derived from polybutene, that is, a polymer of $C_4$ olefins, including 1-butene, 2-butene and isobutylene. Those derived from isobutylene, i.e., polyisobutylenes, are especially preferred. In another preferred embodiment, R is derived from polypropylene. In another preferred embodiment, R is derived from ethylene-alpha olefin polymers, particularly ethylene-propylene-diene polymers. Molecular weights of such polymers may vary over a wide range, but especially preferred are those having number average molecular weights ($M_n$) ranging from about 300 to about 20,000, preferably 700 to about 5000. In one preferred embodiment, the olefin is an ethylene-propylene-diene copolymer having $M_n$ ranging from about 900 to about 2500. An example of such materials are the Trilene® polymers marketed by the Uniroyal Company, Middlebury, Conn., USA.

A preferred source of hydrocarbyl groups R are polybutenes obtained by polymerization of a $C_4$ refinery stream having a butene content of 35 to 75 weight percent and isobutylene content of 15 to 60 weight percent in the presence of a Lewis acid catalyst such as aluminum trichloride or boron trifluoride. These polybutenes contain predominantly (greater than 80% of total repeating units) isobutylene repeating units of the configuration

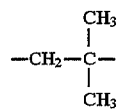

These polybutenes are typically monoolefinic, that is they contain but one olefinic bond per molecule.

The olefinic compound may be a polyolefin comprising a mixture of isomers wherein from about 50 percent to about 65 percent are tri-substituted olefins wherein one substituent contains from 2 to about 500 carbon atoms, often from about 30 to about 200 carbon atoms, more often from about 50 to about 100 carbon atoms, usually aliphatic carbon atoms, and the other two substituents are lower alkyl.

When the olefin is a tri-substituted olefin, it frequently comprises a mixture of cis- and trans- 1-lower alkyl, 1-(aliphatic hydrocarbyl containing from 30 to about 100 carbon atoms), 2-lower alkyl ethene and 1,1-all-lower alkyl, 2-(aliphatic hydrocarbyl containing from 30 to about 100 carbon atoms) ethene.

In one embodiment, the monoolefinic groups are predominantly vinylidene groups, i.e., groups of the formula

especially those of the formula

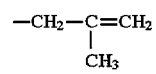

although the polybutenes may also comprise other olefinic configurations.

In one embodiment the polybutene is substantially monoolefinic, comprising at least about 30 mole %, preferably at least about 50 mole % vinylidene groups, more often at least about 70 mole % vinylidene groups. Such materials and methods for preparing them are described in U.S. Pat. Nos. 5,286,823 and 5,408,018, which are expressly incorporated herein by reference. They are commercially available, for example under the tradenames Ultravis (BP Chemicals) and Glissopal (BASF).

As is apparent from the foregoing, olefins of a wide variety of type and of molecular weight are useful for preparing the compositions of this invention. Useful olefins are usually substantially hydrocarbon and have number average molecular weight ranging from about 100 to about 70,000, more often from about 200 to about 7,000, even more often from about 1,300 to about 5,000, frequently from about 400 to about 3,000.

Specific characterization of olefin reactants (A) used in the processes of this invention can be accomplished by using techniques known to those skilled in the art. These techniques include general qualitative analysis by infrared and determinations of average molecular weight, e.g., $M_n$, number average molecular weight, etc., employing vapor phase osmometry (VPO) and gel permeation chromatography (GPC). Structural details can be elucidated employing proton and carbon 13 ($C^{13}$) nuclear magnetic resonance (NMR) techniques. NMR is useful for determining substitution characteristics about olefinic bonds, and provides some details regarding the nature of the substituents. More specific details regarding substituents about the olefinic bonds can be obtained by cleaving the substituents from the olefin by, for example, ozonolysis, then analyzing the cleaved products, also by NMR, GPC, VPO, and by infra-red analysis and other techniques known to the skilled person.

(B) The Carboxylic Reactant

The carboxylic reactant is at least one member selected from the group consisting of compounds of the formula

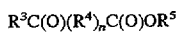

$$R^3C(O)(R^4)_nC(O)OR^5 \quad (IV)$$

and compounds of the formula

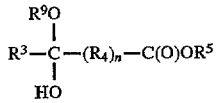

(V)

wherein each of $R^3$, $R^5$ and $R^9$ is independently H or a hydrocarbyl group, $R^4$ is a divalent hydrocarbylene group, and n is 0 or 1. Specific embodiments of the groups $R^3$ and $R^5$ are set forth hereinabove where corresponding groups in the compound (I) are described. $R^9$ is H or hydrocarbyl, preferably H or lower alkyl.

Examples of carboxylic reactants (B) are glyoxylic acid, and other omega-oxoalkanoic acids, keto alkanoic acids such as pyruvic acid, levulinic acid, ketovaleric acids, ketobutyric acids and numerous others. The skilled worker, having the disclosure before him, will readily recognize the appropriate compound of formula (V) to employ as a reactant to generate a given intermediate. Preferred compounds of formula (V) are those that will lead to preferred compounds of formula (I).

Reactant (B) may be a compound of the formula

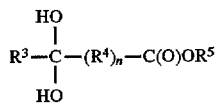

(VII)

wherein each of $R^3$ and $R^5$ is independently H or alkyl. Such compounds arise when the carbonyl reactant is hydrated. Glyoxylic acid monohydrate is a representative example.

From the foregoing, it is apparent that the various 'R' groups in the product (I) correspond to or are derived from corresponding groups in the olefinic and carboxylic reactants.

The process of this invention is conducted at temperatures ranging from ambient up to the lowest decomposition temperature of any of the reactants, usually from about 60° C. to about 220° C., more often from about 120° C. to about 180° C., preferably up to about 160° C. The process employs more than 1.5 moles, preferably from about 1.6 to about 3 moles of reactant (B) per equivalent of reactant (A), more often from about 1.8 to about 2.5 moles of (B) per equivalent of (A) and preferably from about 1.9 to about 2.1 moles (B) per equivalent of (A).

The Compounds

In another embodiment, this invention relates to a composition comprising regioisomers selected from the group consisting of compounds of the formula

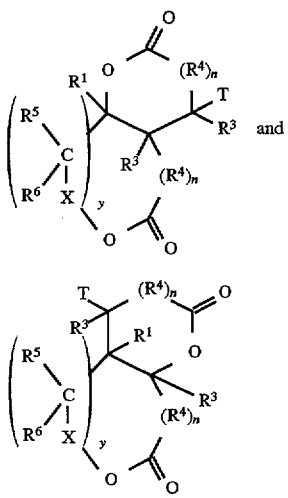

wherein y=0 or 1, n=0 or 1 and X is a divalent hydrocarbyl group selected from the group consisting of
>$C(R^6)(C(R^5)(R^7)(R^8))$ when y=0, and
>$C(R^7)(R^8)$ when y=1, and
T is selected from the group consisting of —OH and $R^5$. More often T is —OH.

Each $R^1$ is independently H or a hydrocarbon based group. In one particular embodiment, each $R^1$ is independently H or a lower alkyl group. As used herein, the expression "lower alkyl" refers to alkyl groups containing from 1 to 7 carbon atoms. Examples include methyl, ethyl and the various isomers of propyl, butyl, pentyl, hexyl and heptyl. In one especially preferred embodiment, each $R^1$ is H.

Each $R^3$ is independently H or hydrocarbyl. These hydrocarbyl groups are usually aliphatic, that is, alkyl or alkenyl, preferably alkyl, more preferably, lower alkyl. Especially preferred is where $R^3$ is H or methyl, most preferably, H.

Each $R^4$ is independently a divalent hydrocarbylene group. This group may be aliphatic or aromatic, but is usually aliphatic. Often, $R^4$ is an alkylene group containing from 1 to about 10 carbon atoms, more often from 1 to about 3 carbon atoms. The 'n' is 0 or 1; that is, in one embodiment, $R^4$ is present and in another embodiment, $R^4$ is absent. More often, $R^4$ is absent.

$R^5$ is H or hydrocarbyl. When $R^5$ is hydrocarbyl, it is usually an aliphatic group, often a group containing from 1 to about 30 carbon atoms, often from 8 to about 18 carbon atoms. In another embodiment, $R^5$ is lower alkyl, wherein "lower alkyl" is defined hereinabove. Most often, $R^5$ is H.

When at least one of $R^6$, $R^7$ and $R^8$ is a hydrocarbyl group, it preferably contains from 7 to about 5,000 carbon atoms. More often, such groups are aliphatic groups. In one embodiment, $R^6$ is an aliphatic group containing from about 10 to about 300 carbon atoms. In another embodiment, $R^6$ contains from 30 to about 100 carbon atoms and is derived from homopolymerized and interpolymerized $C_{2-18}$ olefins.

In a further embodiment, at least one of $R^7$ and $R^8$ is an aliphatic group containing from 10 to about 300 carbon atoms. Often, at least one of $R^7$ and $R^8$ contains from about 30 to about 100 carbon atoms and is derived from homopolymerized and interpolymerized $C_{2-18}$ olefins. The polymerized olefins are frequently 1-olefins, preferably ethylene, propylene, butenes, isobutylene and mixtures thereof. Polymerized olefins are frequently referred to herein as polyolefins.

In yet another embodiment at least one of $R^7$ and $R^8$ is an aliphatic group containing from 8 to about 24 carbon atoms. In another embodiment at least one $R^7$ and $R^8$ is an aliphatic group containing 12 to about 50 carbon atoms. Within this embodiment, most often one of $R^7$ and $R^8$ is H and the other is the aliphatic group.

In one preferred embodiment, each of $R^1$, and $R^3$ is independently hydrogen or a lower alkyl or alkenyl group. In one especially preferred embodiment, each of $R^1$ and $R^3$ is hydrogen and each of y and n=0.

In another preferred embodiment, $R^6$ is an aliphatic group containing from about 8 to about 150 carbon atoms, $R^5$ is H, n is 0 and $R^3$ is H.

The following examples are intended to illustrate several compositions of this invention as well as means for preparing same. Unless indicated otherwise all parts are parts by weight. It is to be understood that these examples are intended to illustrate several compositions and procedures of the invention and are not intended to limit the scope of the invention.

Example 1

A reactor is charged with 450 parts of polyisobutene having $M_n$ about 1000 and 92 parts 50% aqueous glyoxylic acid. The materials are heated under $N_2$ at 200° C. to 205° for 36 hours while collecting 35 parts distillate in a DeareStark trap. The materials are stripped to 180° C. at 2 mm Hg pressure for 1 hour, then are filtered at 150° C. with a diatomaceous earth filter aid. Infrared spectrum shows prominent C=O absorption. saponification No.=36. Total acid No.=5.5

Example 2

A reactor is charged with 380 parts polyisobutene having $M_n$ about 1000 and 75 parts glyoxylic acid monohydrate. The materials are heated under $N_2$ at 200°–210° C. for 7 hours while collecting aqueous distillate in a Dean-Stark trap. The materials are filtered at 150°–160° C. with a diatomaceous earth filter aid.

Example 3

A reactor is charged with 300 parts polyisobutene (CE5203, BASF) having a $M_n$ about 1000 and containing about 49 mole % terminal vinylidene groups, 88.8 parts 50% aqueous glyoxylic acid and 1 part sulfuric acid and a few drops of silicone antifoam agent. Under $N_2$, the materials are heated to 100° C. and held at 100° C. for 1 hour, then to 125° C. and held at 125° C. for 2 hours, then heated to 150° C. and maintained at 150° C. for 3 hours, collecting a total of 49 parts distillate in a Dean-Stark trap. The materials are filtered at 150° C. with a diatomaceous earth filter aid. Saponification No.+71.4; total acid no.=27, 7% unreacted polyisobutene determined by thin layer chromatography using a flame ionization detector (TLC-FID)

Example 4

A reactor is charged with 1360 parts polyisobutene (Glissopal ES3250) having $M_n$ about 1000 and containing about 87 mole percent terminal vinylidene groups, 250 parts glyoxylic acid monohydrate and 1.35 parts 70% aqueous methane sulfonic acid. The materials are heated under $N_2$ for 4 hours at 155°–160° C. while collecting 82 parts aqueous distillate in a Dean-Stark trap. The materials are filtered at 155°–160° C. with a diatomaceous earth filter aid. Infra red spectrum: very strong lactone C=O at 1774 cm$^{-1}$. Saponification No. +107; Total acid no+31.8, 9% unreacted polyisobutene (TLC-FID).

Example 5

A reactor is charged with 500 parts of the polyisobutene of Example 3 and 148 parts 50% aqueous glyoxylic acid. The materials are heated to 150° and held at 150° for 3 hours while removing aqueous distillate. Unreacted polyisobutylene (TLC-FID)+29.2% The materials are mixed at 150° with 144 parts mineral oil diluent the solution is filtered employing a diatomaceous earth filter aid. Saponification No.=46; total acid No.=13.

Example 6

To a reactor are charged 1000 parts of the polyisobutene of Example 4, 296 parts 50% aqueous glyoxylic acid and a few drops silicone antifoam agent. The mixture is heated to 160° and is held at 160° for 16 hours while removing aqueous distillate. The material contains by TLC-FID 22% unreacted polyisobutene. Diluent oil, 287 parts, is added, the materials are heated to 110° C. and filtered with a diatomaceous earth filter aid. Saponification No.=57, Total acid no.=11.5.

Example 7

A reactor is charged with 300 parts polyisobutene (Glissopal ES 3252, BASF) having $M_n$ about 2400 and containing about 70 mole percent terminal vinylidene groups and 35.8 parts 50% aqueous glyoxylic acid. The materials are heated to 160° C. and are held at 160° C. for 16 hours. Unreacted polyisobutene (TLC-FID)=24%. Mineral oil diluent, 84 parts, is added and the materials are mixed at 110° C. the filtered with a diatomaceous earth filter aid. Saponification No.=22.4,Total acid No.=6.9.

Example 8

A reactor is charged with 500 parts of polyisobutene (Ultravis 10, BP Chemicals) having $M_n$ about 1000 which is heated to 100° C., then 9 parts 70% aqueous methanesulfonic acid are added followed by dropwise addition of 148 parts 50% aqueous glyoxylic acid over 0.5 hour. The temperature is increased to 150° C. and the materials are held at 150° C. over 12 hours. TLC-FID analysis shows 10.6% unreacted polyisobutene. The materials are mixed with 144 parts mineral oil diluent and filtered with a diatomaceous earth filter aid. Saponification no.=44, total acid no.=17.5.

Example 9

The procedure of Example 1 is repeated replacing the polyisobutylene with an equivalent amount, based on C=C, of $C_{16-18}$ alpha olefin.

Example 10

The procedure of Example 2 is repeated replacing the polyisobutylene with equivalent amounts (based on C=C) of $C_{24-28}$ alpha olefin.

Example 11

The procedure of Example 1 is repeated replacing glyoxylic acid with an equivalent amount, based on —COOH, of pyruvic acid.

Example 12

The procedure of Example 1 is repeated replacing glyoxylic acid with an equivalent amount (based on COOH) of levulinic acid.

Example 13

A reactor is charged with 3000 parts of polyisobutylene having a number average molecular weight of about 2400 (Glissopal ES 3252, BASF), 230.3 parts glyoxylic acid monohydrate, 17.5 parts 70% aqueous methane sulfonic acid and a few drops of a silicone antifoam agent. The materials are heated under $N_2$ purge (0.3 cubic feet per hour) to 130° C. and then are heated at 130° C. for a total of 11 hours while collecting a total of 140 parts aqueous distillate. The materials are cooled to room temperature, 2093 parts mineral oil diluent are added and the solution is stirred while heating to 130° C. whereupon the solution is filtered with a diatomaceous earth filter aid. Saponification no.=20.2; Total acid no.=6.7. Unreacted polyisobutylene=11% (TLC-FID).

While the invention has been explained in relation to its preferred embodiments, it is to be understood that various modifications thereof will become apparent to those skilled in the art upon reading the specification. Therefore, it is to be understood that the invention disclosed herein is intended to cover such modifications that fall within the scope of the appended claims.

What is claimed is:

1. A composition comprising compounds of the formula wherein n=0; y=0 or 1;
wherein X is a divalent hydrocarbyl group selected from the group consisting of
> $C(R^6)(C(R^5)(R^7)(R^8))$ when y=0, and
> $C(R^7)(R^8)$ when y=1
wherein $R^1$ is H or a hydrocarbon based group;
each $R^3$ is independently H or hydrocarbyl;
each $R^4$ is independently a divalent hydrocarbylene group;
$R^5$ is H or hydrocarbyl;
each of $R^6$, $R^7$ and $R^8$ is independently H or a hydrocarbon based group, and T is —OH.

2. The composition of claim 1 wherein each of $R^1$ and $R^3$ is independently H or a lower alkyl or alkenyl group.

3. The composition of claim 1 wherein each of $R^1$ and $R^3$ is H.

4. The composition of claim 1 wherein X has the formula

> $C(R^7(R^8)$—.

5. The composition of claim 1 wherein X has the formula

> $C(R^6)(C(R^5)(R^7)(R^8))$.

6. The composition of claim 1 wherein at least one of $R^1$ $R^6$ $R^7$, and $R^8$ is a hydrocarbyl group containing from about 7 to about 5000 carbon atoms.

7. The composition of claim 6 wherein $R^6$ is an aliphatic group containing from about 10 to about 300 carbon atoms.

8. The composition of claim 7 wherein $R^6$ contains from 30 to about 100 carbon atoms and is derived from a polymer selected from the group consisting of homopolymerized and interpolymerized $C_{2-10}$ olefins.

9. The composition of claim 6 wherein at least one of $R^7$ and $R^8$ is an aliphatic group containing from about 10 to about 300 carbon atoms.

10. The composition of claim 9 wherein at least one of $R^7$ and $R^8$ contains from about 30 to about 100 carbon atoms and is derived from a polymer selected from the group consisting of homopolymerized and interpolymerized $C_{2-10}$ olefins.

11. The composition of claim 8 wherein the olefins are 1-olefins.

12. The composition of claim 11 wherein the 1-olefins are ethylene, propylene, butene, isobutylene and mixtures thereof.

13. The composition of claim 12 wherein the 1-olefin is isobutylene.

14. The composition of claim 10 wherein the olefins are ethylene, propylene, butenes and mixtures thereof.

15. The composition of claim 1 wherein at least one of $R^7$ and $R^8$ is an aliphatic group containing from 8 to about 24 carbon atoms.

16. The composition of claim 1 wherein at least one of $R^7$ and $R^8$ contains from 12 to about 50 carbon atoms.

17. The composition of claim 1 wherein $R^6$ is an aliphatic group containing from 8 to about 24 carbon atoms.

18. The composition of claim 1 wherein $R^6$ contains from 12 to about 50 carbon atoms.

19. The composition of claim 1 wherein $R^1$ is H or lower alkyl.

20. The composition of claim 19 wherein one of $R^1$ and $R^3$ is H and the other is lower alkyl.

21. The composition of claim 3 wherein $R^6$ is an aliphatic group containing from about 8 to about 150 carbon atoms.

22. The composition of claim 1 wherein $R^5$ is H or a lower alkyl group.

23. A composition comprising compounds of the formula wherein n=0; y=;
wherein X is a divalent hydrocarbyl group selected from the group consisting of

> $C(R^7)(R^8)$ wherein $R^1$ is H or a hydrocarbon based group;
each $R^3$ is independently H or hydrocarbyl;
$R^5$ is H or hydrocarbyl;
each of $R^6$, $R^7$ and $R^8$ is independently H or a hydrocarbon based group, and T is selected from the group consisting of —OH and $R^5$.

24. The composition of claim 23 wherein each of $R^1$ and $R^3$ is independently H or a lower alkyl or alkenyl group.

25. The composition of claim 24 wherein each of $R^1$ and $R^3$ is H.

26. The composition of claim 23 wherein at least one of $R^1$, $R^6$, $R^7$, and $R^8$ is a hydrocarbyl group containing from about 7 to about 5000 carbon atoms.

27. The composition of claim 26 wherein $R^6$ is an aliphatic group containing from about 10 to about 300 carbon atoms.

28. The composition of claim 27 wherein $R^6$ contains from 30 to about 100 carbon atoms and is derived from a polymer selected from the group consisting of homopolymerized and interpolymerized $C_{2-10}$ olefins.

29. The composition of claim 26 wherein at least one of $R^7$ and $R^8$ is an aliphatic group containing from about 10 to about 300 carbon atoms.

30. The composition of claim 29 wherein at least one of $R^7$ and $R^8$ contains from about 30 to about 100 carbon atoms and is derived from a polymer selected from the group consisting of homopolymerized and interpolymerized $C_{2-10}$ olefins.

31. The composition of claim 28 wherein the olefins are 1-olefins.

32. The composition of claim 31 wherein the 1-olefins are ethylene, propylene, butene, isobutylene and mixtures thereof.

33. The composition of claim 32 wherein the 1-olefin is isobutylene.

34. The composition of claim 30 wherein the olefins are ethylene, propylene, butenes and mixtures thereof.

35. The composition of claim 23 wherein at least one of $R^7$ and $R^8$ is an aliphatic group containing from 8 to about 24 carbon atoms.

36. The composition of claim 23 wherein at least one of $R^7$ and $R^8$ contains from 12 to about 50 carbon atoms.

37. The composition of claim 23 wherein $R^6$ is an aliphatic group containing from 8 to about 24 carbon atoms.

38. The composition of claim 23 wherein $R^6$ contains from 12 to about 50 carbon atoms.

39. The composition of claim 23 wherein $R^1$ is H or lower alkyl.

40. The composition of claim 39 wherein one of $R^1$ and $R^3$ is H and the other is lower alkyl.

41. The composition of claim 26 wherein $R^6$ is an aliphatic group containing from about 8 to about 150 carbon atoms.

42. The composition of claim 23 wherein $R^5$ is H or a lower alkyl group.

43. A composition comprising compounds of the formula

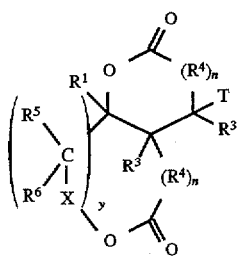

wherein n=0; y=0 or 1;

wherein X is a divalent hydrocarbyl group selected from the group consisting of $>C(R^6)(C(R^5)(R^7)(R^8))$ when y=0, and $>C(R^7)(R^8)$ when y=1 wherein $R^1$ is H or a hydrocarbon based group;

each $R^3$ is independently H or hydrocarbyl;

each $R^4$ is independently a divalent hydrocarbylene group;

$R^5$ is H or hydrocarbyl, wherein $R^6$ contains from 30 to about 100 carbon atoms and is derived from a polymer selected from the group consisting of homopolymerized and interpolymerized $C_{2-10}$ olefins;

each of $R^7$ and $R^8$ is independently H or a hydrocarbon based group, and T is selected from the group consisting of —OH and $R^5$.

44. The composition of claim 43 wherein each of $R^1$ and $R^3$ is independently H or a lower alkyl or alkenyl group.

45. The composition of claim 43 wherein each of $R^1$ and $R^3$ is H.

46. The composition of claim 43 wherein X has the formula $>C(R^7)(R^8)$—.

47. The composition of claim 43 wherein X has the formula $>C(R^6)(C(R^5)(R^7)(R^8))$.

48. The composition of claim 43 wherein the olefins are 1-olefins.

49. The composition of claim 48 wherein the 1-olefin is isobutylene.

50. The composition of claim 43 wherein $R^5$ is H or a lower alkyl group.

51. A composition comprising compounds of the formula

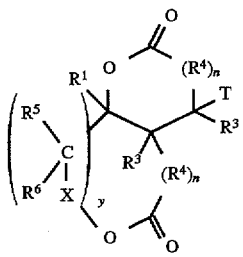

wherein n=0; y=0 or 1;

wherein X is a divalent hydrocarbyl group selected from the group consisting of $>C(R^6)(C(R^5)(R^7)(R^8))$ when y=0, and $>C(R^7)(R^8)$ when y=1 wherein $R^1$ is H or a hydrocarbon based group;

each $R^3$ is independently H or hydrocarbyl;

each $R^4$ is independently a divalent hydrocarbylene group;

$R^5$ is H or hydrocarbyl;

$R^6$ is H or a hydrocarbon based group, wherein at least one of $R^7$ and $R^8$ contains from about 30 to about 100 carbon atoms and is derived from a polymer selected from the group consisting of homopolymerized and interpolymerized $C_{2-10}$ olefins.

52. The composition of claim 51 wherein each of $R^1$ and $R^3$ is independently H or a lower alkyl or alkenyl group.

53. The composition of claim 51 wherein each of $R^1$ and $R^3$ is H.

54. The composition of claim 51 wherein X has the formula $$>C(R^7(R^8)-.$$

55. The composition of claim 51 wherein X has the formula $$>C(R^6)(C(R^5(R^{7)(R8)})).$$

56. The composition of claim 51 wherein the olefins are 1-olefins.

57. The composition of claim 56 wherein the 1-olefin is isobutylene.

58. The composition of claim 51 wherein $R^5$ is H or a lower alkyl group.

* * * * *